(12) United States Patent
Sriram

(10) Patent No.: US 11,013,449 B2
(45) Date of Patent: May 25, 2021

(54) METHODS AND SYSTEMS FOR DECODING, INDUCING, AND TRAINING PEAK MIND/BODY STATES VIA MULTI-MODAL TECHNOLOGIES

(71) Applicant: Roshan Narayan Sriram, Saratoga, CA (US)

(72) Inventor: Roshan Narayan Sriram, Saratoga, CA (US)

( * ) Notice: Subject to any disclaimer, the term of this patent is extended or adjusted under 35 U.S.C. 154(b) by 0 days.

(21) Appl. No.: 16/418,805

(22) Filed: May 21, 2019

(65) Prior Publication Data

US 2019/0269345 A1    Sep. 5, 2019

(51) Int. Cl.
| | |
|---|---|
| *A61B 5/0482* | (2006.01) |
| *A61B 5/0205* | (2006.01) |
| *A61B 5/16* | (2006.01) |
| *A61B 5/00* | (2006.01) |
| *A61M 21/02* | (2006.01) |
| *A61B 5/053* | (2021.01) |
| *A61B 5/11* | (2006.01) |
| *A61B 5/0404* | (2006.01) |
| *A61M 21/00* | (2006.01) |
| *A61B 5/375* | (2021.01) |

(Continued)

(52) U.S. Cl.
CPC ............ *A61B 5/375* (2021.01); *A61B 5/0205* (2013.01); *A61B 5/165* (2013.01); *A61B 5/6803* (2013.01); *A61B 5/7267* (2013.01); *A61M 21/02* (2013.01); *A61B 5/0533* (2013.01); *A61B 5/1102* (2013.01); *A61B 5/332* (2021.01); *A61M 2021/005* (2013.01); *A61M 2021/0027* (2013.01); *A61M 2205/3303* (2013.01)

(58) Field of Classification Search
CPC ... A61B 5/0482; A61B 5/0404; A61B 5/0205; A61B 5/165; A61B 5/6803; A61B 5/7267; A61B 5/0533; A61B 5/1102; A61M 21/02; A61M 2021/0027; A61M 2021/005; A61M 2205/3303
See application file for complete search history.

(56) References Cited

U.S. PATENT DOCUMENTS

| | | | |
|---|---|---|---|
| 2011/0041086 A1* | 2/2011 | Kim .................. | G06F 3/0488 715/764 |
| 2014/0066798 A1* | 3/2014 | Albert ................ | A61B 5/0452 600/513 |

(Continued)

*Primary Examiner* — Christopher Koharski
*Assistant Examiner* — Amanda L Steinberg
(74) *Attorney, Agent, or Firm* — Barry Choobin; Patent 360

(57) ABSTRACT

Presented here is a system and method for monitoring, analyzing, and inducing peak mental states. Brainwave sensors are placed on the scalp of the user to measure the user's mental state. A machine learning model can interpret the measured brainwave signals into a mental state of the user, such as relaxed, focused, stressed, happy, sad, etc. the system can obtain a desired mental state of the user, such as relaxed, etc. The system can measure the difference between the desired mental state and the measured mental state of the user and provide audio and visual feedback to the user indicating how far the user is from the desired mental state. Further, the system can provide audio and visual feedback to help or challenge the user in reaching the desired mental state. The visual and audio feedback can be provided using a virtual reality and/or an augmented reality product.

16 Claims, 12 Drawing Sheets

(51) Int. Cl.
  *A61B 5/0533* (2021.01)
  *A61B 5/332* (2021.01)

(56) References Cited

U.S. PATENT DOCUMENTS

| | | | | |
|---|---|---|---|---|
| 2014/0267005 | A1* | 9/2014 | Urbach | G06F 3/016 345/156 |
| 2014/0347265 | A1* | 11/2014 | Aimone | G09G 3/003 345/156 |
| 2015/0351655 | A1* | 12/2015 | Coleman | A61B 5/0482 600/301 |
| 2016/0267809 | A1* | 9/2016 | deCharms | A61B 3/113 |

* cited by examiner

| Plan | Description |
|---|---|
| Meditation Module 800 | Analyzes data from EEG device and guides user s meditation accordingly |
| Cognitive Health Tracking Module 810 | Records users cognitive health (attention, memory, learning) over a monthly period and provides analysis, tips, journal |
| Emotion Health Tracking Module 820 | Records users mental health (emotions, stressors) over a monthly period and provides analysis, tips, journal |
| Recovery/Skill Mastery 830 | Addresses specific mental or cognitive health goal with emotion and cognitive health tracking and provides further guidance and analysis focused on health goal |

FIG. 8

| Customer Segment | Limitations of Current Solution | Value Differentiation |
|---|---|---|
| Meditators | Meditation apps are gimmicky and are not rooted in scientifically tested and validated methods | More precise neurofeedback – integrating audio and visual feedback – better guided sessions – more personalized |
| Corporate Wellness (First Market) | Organizations don t have a direct way of assessing performance or providing effective interventions for improving performance | Tracking and measuring performance changes, mood changes – Lower stress |
| Institutional Wellness | Educational institutions don t have a direct way of assessing performance or providing effective interventions for improving performance | Better performance on standardized tests (SAD, GMAT), grades, job placement – lower stress, better mood |
| PTSD | PTSD treatment is too costly and ineffective | Lesser the frequency, duration, and strength of their flashback episodes – emotional healing – improved day to day life |
| Alzheimer s | Alzheimer s treatment is too costly and ineffective | Better cognitive performance (memory, attention, learning) – improved day to day life |
| Athletes | Lack of technology to quantify athletic performance and improve mental resilience and readiness of athlete | Better mental fitness and better overall performance |

FIG. 9

METHODS AND SYSTEMS FOR DECODING, INDUCING, AND TRAINING PEAK MIND/BODY STATES VIA MULTI-MODAL TECHNOLOGIES

CROSS-REFERENCE TO RELATED APPLICATIONS

This application claims priority to the U.S. provisional patent application Ser. No. 62/592,560 filed Nov. 30, 2017 which is incorporated herein by reference in its entirety.

TECHNICAL FIELD

The present application is related to bio-signals, such as brainwaves, and, more specifically, to methods and systems that provide audio and visual feedback to monitor, analyze, train and induce peak mental states based on brainwaves.

BACKGROUND

Existing technology-based meditation applications are designed for relaxation & de-stress purposes, using closed eye guided meditations, biofeedback guided meditations or open eye VR guided meditations. While meditation can be mildly effective for utilities, such as enhancing mental performance, by increasing an individual's focus, confidence and energy to get into the flow state or "zone", no technology-based meditation application exists to repeatedly and efficiently induce meditative states that can aid in peak performance. In order to access hyper-performance mental states through meditation, aspirants have had to practice for decades, without the aid of quantitative progression and evaluation metrics. With the advent of the technology proposed, we are enabling individuals to bypass years of training to gain access and control of peak mental states in order to unlock accelerated, quantified, immediate, and sustainable performance improvements.

SUMMARY

Presented here is a neurofeedback system and method for monitoring, analyzing, training and inducing peak mental states. An EEG headband worn by the user to measure the user's mental state. A machine learning model can interpret the measured signals into a mental state of the user, such as relaxed, focused, stressed, happy, sad, energetic etc. The system can obtain a desired mental state of the user, such as relaxed, energized etc. The system can measure the difference between the desired mental state and the measured mental state of the user and provide audio and visual feedback to the user indicating how far the user is from the desired mental state. Further, the system can provide audio and visual feedback to help or challenge the user in reaching the desired mental state. The visual and audio feedback can be provided using a virtual reality and/or an augmented reality product.

BRIEF DESCRIPTION OF THE DRAWINGS

FIG. 8 shows various services provided by the system.

FIG. 9 shows a value differentiation of the current system.

DETAILED DESCRIPTION

Immersive Audio and Visual Feedback Based on Brainwaves to Train, Monitor, Analyze, and Induce Peak Mental States Presented here is a system and method for monitoring, analyzing and inducing peak mental states. A brainwave sensor placed on the scalp of the user can measure the user's brainwaves. Other sensors, such as Galvanic Skin Response, Electrocardiograms, Seismocardiogram, and Ballistocardiogram sensors can be worn by the user. A machine learning model can interpret the measured bio-signals into a mental state of the user, such as relaxed, focused, stressed, happy, sad, etc. The system can obtain a desired mental state of the user, such as relaxed, etc. The system can measure the difference between the desired mental state and the measured mental state of the user and provide audio and visual feedback to the user indicating how far the user is from the desired mental state. Further, the system can provide audio and visual feedback to help or challenge the user in reaching the desired mental state. The visual and audio feedback can be provided using a virtual reality and/or an augmented reality product.

Figure 1:
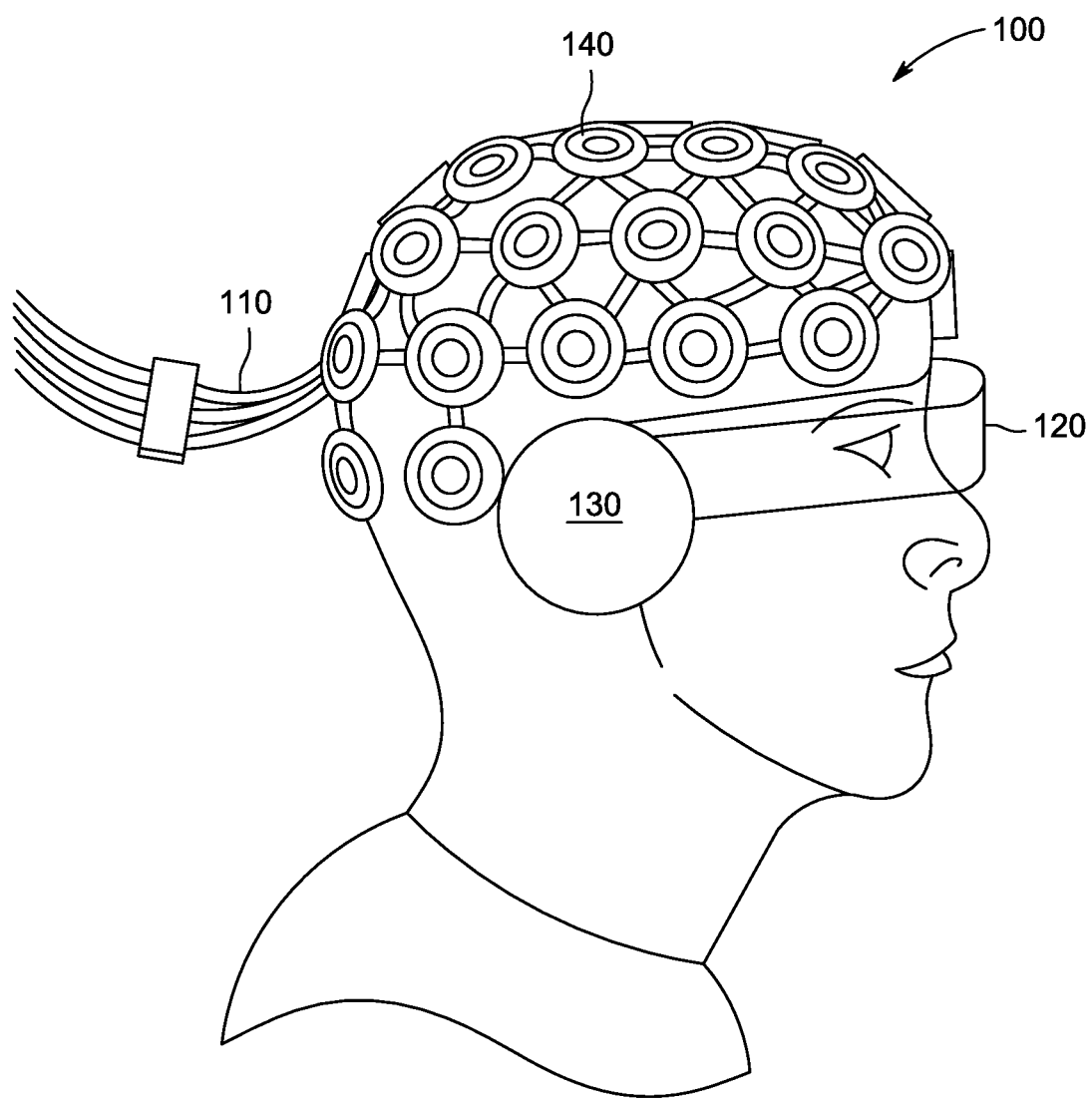
FIG. 1 shows a user connected to a sensor detecting brainwave signals.

FIG. 1 shows a user connected to a sensor detecting brainwave signals. The system 100 can include the sensor 110 to detect brainwave signals, a display 120 to provide visual feedback to the user, and an audio emitter 130 to provide audio feedback to the user. The display 120 can be associated with a virtual reality (VR) headset, as shown in FIG. 1, or can be a computer monitor, a mobile device display, an augmented reality (AR) headset, such as smart glasses, etc. The audio emitter 130 can be a speaker built into the display 120, such as the VR headset, AR headset, or can be a separate speaker electrically connected to the display 120.

The sensor 110 can include multiple electrodes 140 (only one labeled for brevity) placed along the scalp of the user and continually detecting electrical activity of the brain. The waveform so produced is the brainwave signal, which can have varying frequencies depending on the user's mental state. The gamma brainwave signal has frequencies in the 30 to 100 Hz range and can occur when the user is in a heightened sense of consciousness, bliss, and intellectual acuity. The beta brainwave signal has frequencies in the 14 to 30 Hz range and can occur when the user is awake and mentally active. The alpha brainwave signal has frequencies in the 8 to 14 Hz range and can be generated when the user is awake and resting. The theta brainwave signal has frequencies in the 3.5 to 8 Hz range and can be generated when the user is sleeping. The delta brainwave has frequencies less than 3.5 Hz and can be generated when the user is in deep sleep.

In a meditative state, increased alpha brainwave signals and gamma brainwave signals occur. For example, when the user closes his\her eyes, there is an increase in the alpha brainwave signal. Further, in deep meditation, the gamma brainwave signal can be detected most commonly around 40 Hz. To encourage the user to reach a desired mental state, such as relaxation meditation, visual feedback and audio feedback can be provided indicating the closeness of the user to the desired mental state. Further, the user can be incentivized to practice reaching and maintaining the desired mental state by tracking the user's past performance in reaching and maintaining the desired mental state.

Figure 2B:
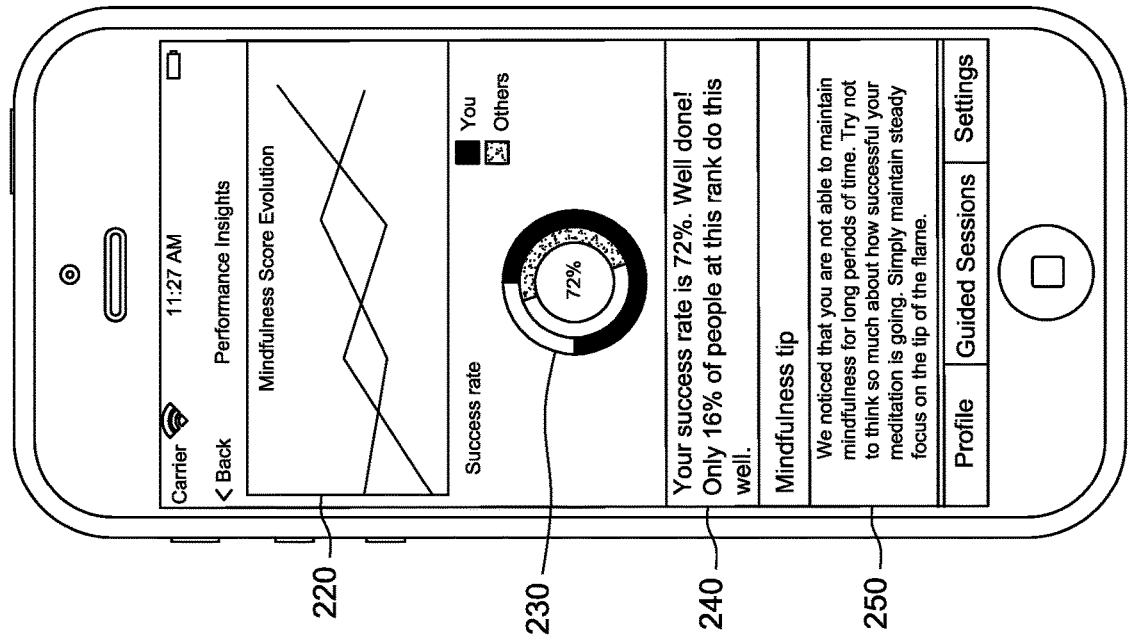
FIG. 2B shows an incentive provided to a user, according to one embodiment.
Figure 2A:
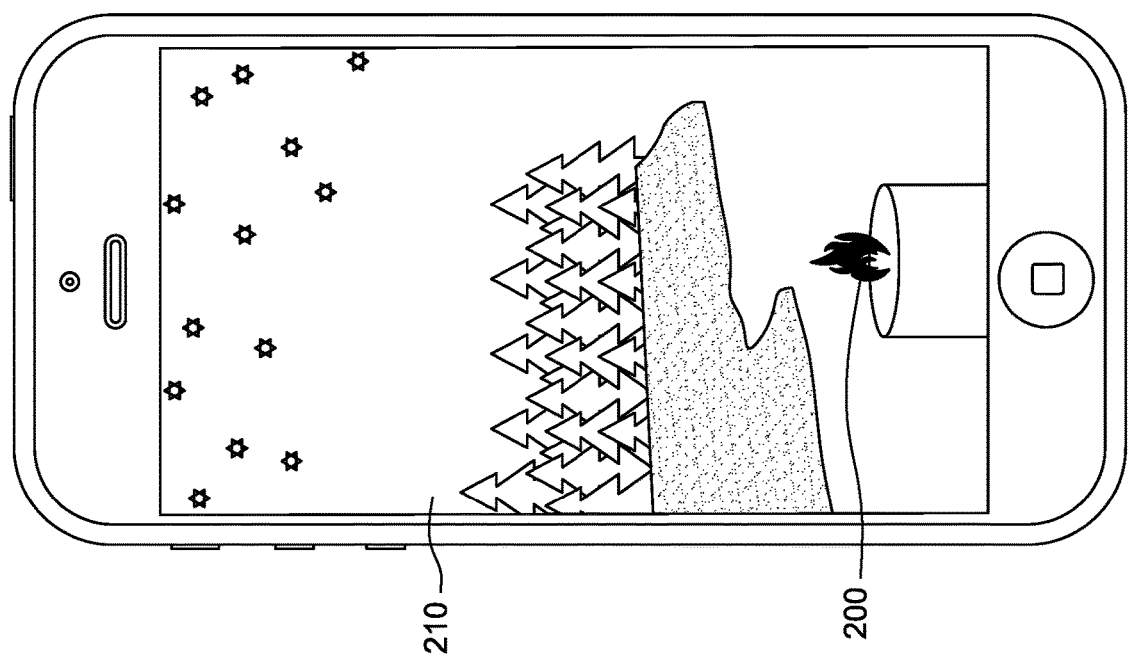
FIG. 2A shows a visual feedback provided to a user, according to one embodiment.

FIG. 2A shows a visual feedback provided to a user, according to one embodiment. The display 120 is associated with the mobile device. The display 120 shows a visual feedback indicating a proximity of the latest determined mental state of the user to the desired mental state of the user. The display 120 can be associated with the mobile device. This visual feedback on display 120 is determined using the sensor 110 in FIG. 1.

The sensor 110 in FIG. 1 can measure the brainwave signal of the user, and a processor (not pictured) associated with the sensor 110 can translate the measured brainwave signal into the mental state of the user. The processor can also obtain the desired mental state of the user, as described further in this application. The mental state can include an emotional state and a cognitive state. The cognitive state can include the user's focus, problem-solving skills, etc., while the emotional state can include the user's stress level, happiness, sadness, etc.

The processor can determine a difference between the desired mental state and the measured mental state of the user and provide visual and/or audio feedback to the user indicating the difference between the two. For example, in FIG. 2A an element of the display, such as the flame 200 or the background 210, can indicate the difference.

For example, focusing can make the flame brighter orange, whereas being distracted can make the flame emerald green or sapphire blue. If the user is too stressed, the weather can be cloudy and raining, whereas if the user is calm, the weather can be peaceful and serene. To have the foreground and background interact, the brighter flames can be more resistant to the weather. Consequently, if a person is both distracted and stressed, the flame can go out and the session can end, or the user can be penalized in terms of the overall score for the session. If the user is focused and stressed, but the user manages to calm down, the user can progress in the game. If the user is relaxed but distracted, the flame can become duller and duller without going out, giving the user the feedback to refocus their attention on the tip of the flame.

In another example, the more focused the user is, the bigger the flame becomes, and the calmer the user is the steadier the flame becomes. In addition, the processor can provide an audio feedback. If the user is distracted, the audio feedback can include sound of wind, and if the user is calmer, the sound of the wind can subside. As the user's mental state approaches the desired mental state, the visual and/or audio feedback can indicate the proximity to the desired mental state by studying the flame and/or reducing the amplitude of the sound of the wind, thus rewarding the user.

FIG. 2B shows an incentive provided to the user, according to one embodiment. The processor can track the user's success in achieving and/or maintaining the desired mental state during multiple sessions. The processor can track various metrics. For example, the processor can track the number of times the user managed to maintain the desired mental state for at least 50% of the session time, or the number of times the user managed to achieve the desired mental state in the last 10 sessions. The tracked metric can be compared to the same tracked metric of other users. The group of other users can be all the users of the application, or other users having a comparable proficiency in controlling their mental state as the current user.

For example, in FIG. 2B the processor tracks the number of times the user managed to achieve a desired level of focus. The processor can provide visual feedback to the user via graphical user interface elements 220, 230, and 240 indicating the user's performance as compared to the other users. Further, the processor can indicate in the graphical user element 250, an area for improvement.

Figure 3B:
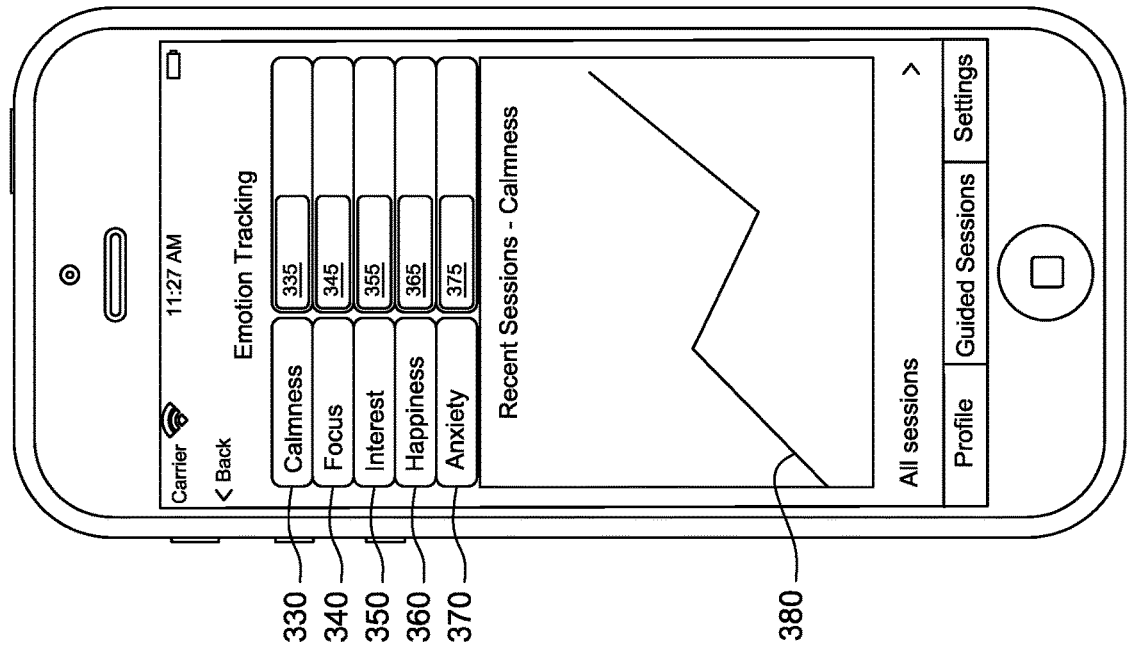
FIG. 3B shows an incentive provided to a user, according to another embodiment.
Figure 3A:
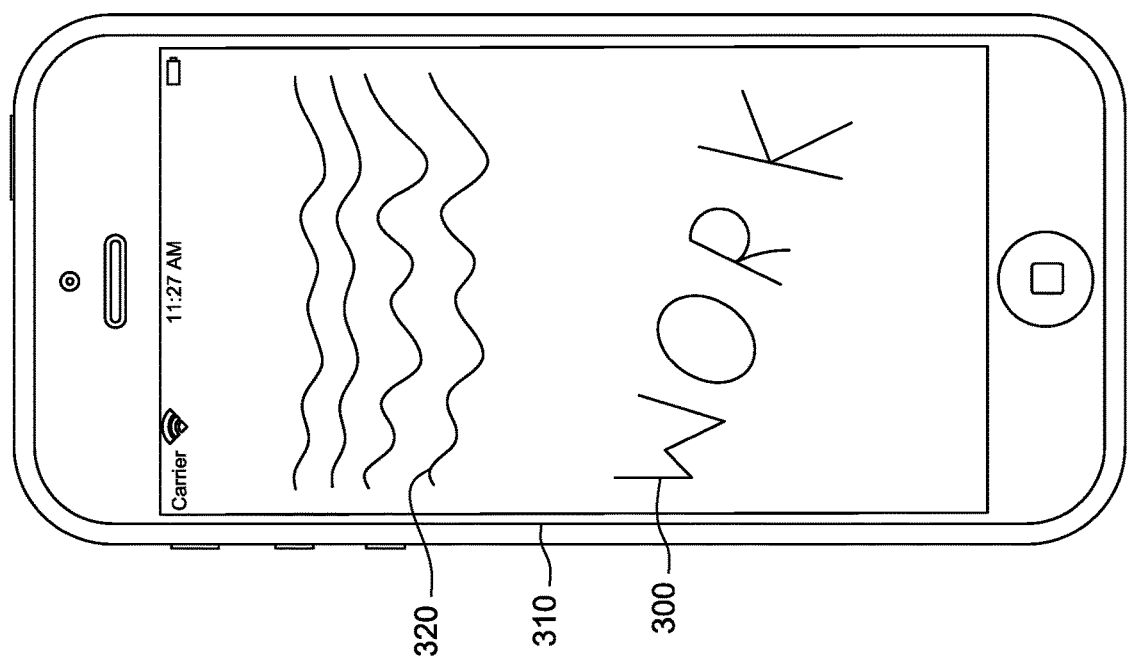
FIG. 3A shows a visual feedback provided to the user, according to another embodiment.

FIG. 3A shows a visual feedback provided to the user, according to another embodiment. The processor can receive from a user words or emojis that correspond to the user's current stressor. The processor can display the current stressor 300 within the display 310. The processor can measure the user's brainwave signal and the proximity of the user's brainwave signal. The distance between the two can be represented as the distance between the current stressor 300 and the waves 320. As the user's brainwave signal gets closer to the desired brainwave signal, the waves 320 can approach the current stressor 300. In effect, the user can move the waves 320 towards the shore.

The weather can be adjusted based on the user's level of relaxation. For example, if the user is too stressed, the weather can take on the quality of a storm and the waves can be harsh. However, as the user starts to relax, the weather can start to calm down and waves can become smooth. The processor can establish a maximum intensity threshold for the negative stimulus to prevent the feedback from overwhelming the user.

The level of focus and relaxation, i.e. the desired mental state, needed to successfully wash away the current stressor 300 can be dynamically adjusted based on the user's mindfulness proficiency, i.e. skill level.

For example, at an easy level, the desired mental state to successfully wash away the current stressor can be computed based on an average ability of novice users; at a medium level, the desired mental state to successfully wash away the current stressor can be computed based on an average ability of users that use the game sporadically; and at a high level the desired mental state to successfully wash away the current stressor can be based on an average ability of users that use the game regularly. In another example, at the easy level, the desired mental state to successfully wash away the current stressor 300 can be achieving the desired mental state for any period of time; the medium level can be to successfully achieve the desired mental state for at least 30% of the time; and the high level can be to successfully achieve the desired mental state for at least 60% of the time.

The current stressor 300 can be partially washed away to indicate the user's progress towards maintaining the desired mental state for the sufficient period of time. At the easy level, just achieving the desired mental state can wash away the current stressor 300 at once. At the medium level and the high level, maintaining the desired mental state for half the time, for example, can halfway wash away the current stressor 300. Upon successfully washing away the current stressor 300, users will be rewarded with soothing sounds and pleasant colors as the waves recede back into the ocean.

FIG. 3B shows an incentive provided to a user, according to another embodiment. The processor can track the user's performance in various mental states, such as calmness 330, focus 340, interests 350, happiness 360, and anxiety 370. The processor can also present a graph 380 representing the user's success in achieving the desired mental state, and/or an amount of time the user has spent in the various mental states 330, 340, 350, 360, and 370. In FIG. 3B, the selected mental state is calmness 330, and the graph 380 represents the amount of time the user has spent being calm.

The user success can be represented as a normalized amount of time the user has spent in the various mental states 330, 340, 350, 360, and 370 as compared to the total amount of time spent in the application. For example, the normalized amount of time can be a percentage, a fraction, etc. of the time the user has spent in the various mental states 330, 340, 350, 360, and 370. The relative size of the bars 335, 345, 355, 365, and 375 can represent a ratio between the normalized amount of time spent in the corresponding mental states 330, 340, 350, 360, and 370.

Figure 4:
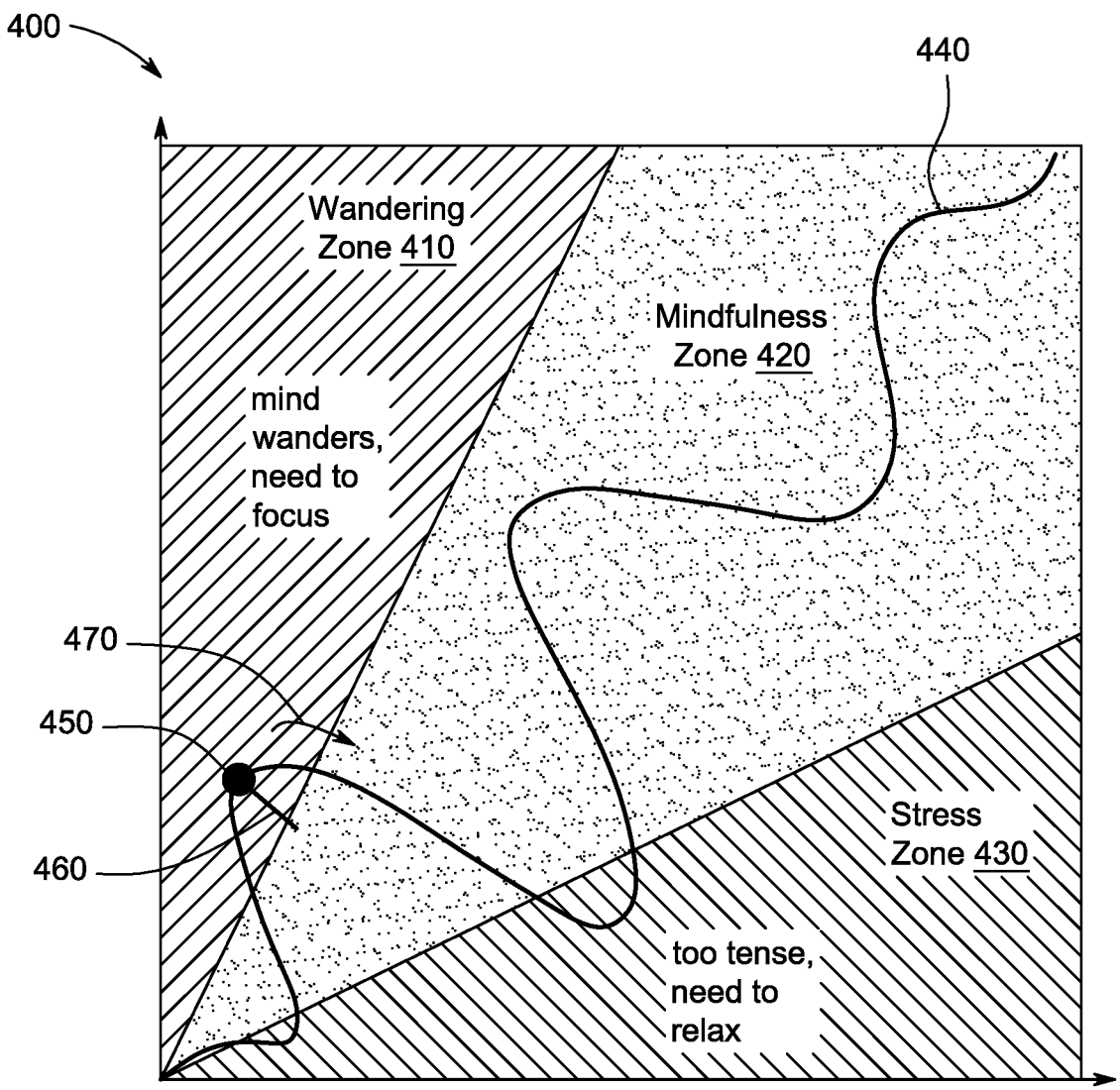
FIG. 4 shows a graph indicating a proximity of a measured mental state to a desired mental state.

FIG. 4 shows a graph indicating the proximity of a measured mental state to a desired mental state. The graph 400 can have at least two axes representing two independent mental states, such as focus and relaxation. The graph 400 can be three or four dimensional, depending on the number of independent mental states measured. Independent mental states require that an intensive experience of one mental state can vary independently of the other mental state. For example, in FIG. 4, the user can be highly focused and not relaxed, not focused and highly relax, etc.

Region 410 of the graph 400 represents a wandering zone when the user is relaxed, but not sufficiently focused. Region 420 represents the mindfulness zone which can be a desired mental state. Region 430 represents the stress zone where the user is highly focused, but not sufficiently relaxed. Curve 440 can represent the continually measured mental state of the user over time. When curve 440 is within the region 420, the user's desired mental state is achieved, and the user can be given visual and audio feedback. For example, the flame 200 in FIG. 2 can become brighter orange and/or steadier, while the waves 320 in FIG. 3A can at least partially wash away the current stressor 300 in FIG. 3A.

To measure the distance of the measured mental state of the user, the processor can determine where within the graph 400 the user's mental state is. For example, the user's measured mental state can be at a position 450. The distance between the user's mental state 450 and the desired mental state can be a length of a segment 460, which represents the shortest distance between the position 450 and the mindfulness zone 420. As the measured mental state of the user moves in the direction 470, the distance between the user's measured mental state in the desired mental state of region 420 decreases, i.e., the proximity between the two increases and the user is rewarded with positive visual and/or audio feedback.

In addition to or instead of providing proximity feedback, the processor can provide the visual and audio feedback to induce the desired state of mind. The processor can increase the loudness of a sound to cause the user to relax. The processor can also increase the intensity and variation in the visual feedback to cause the user to increase focus.

For example, if the measured user's mental state is at position 450, the processor can determine that the user needs to focus more, and as a result the processor can increase the intensity and/or variation in the visual feedback. For example, in case of the flame 200 in FIG. 2, the processor can provide an unsteady, flickering flame. The processor can also determine that the user is too relaxed and consequently decrease intensity of the sound.

Figure 5:
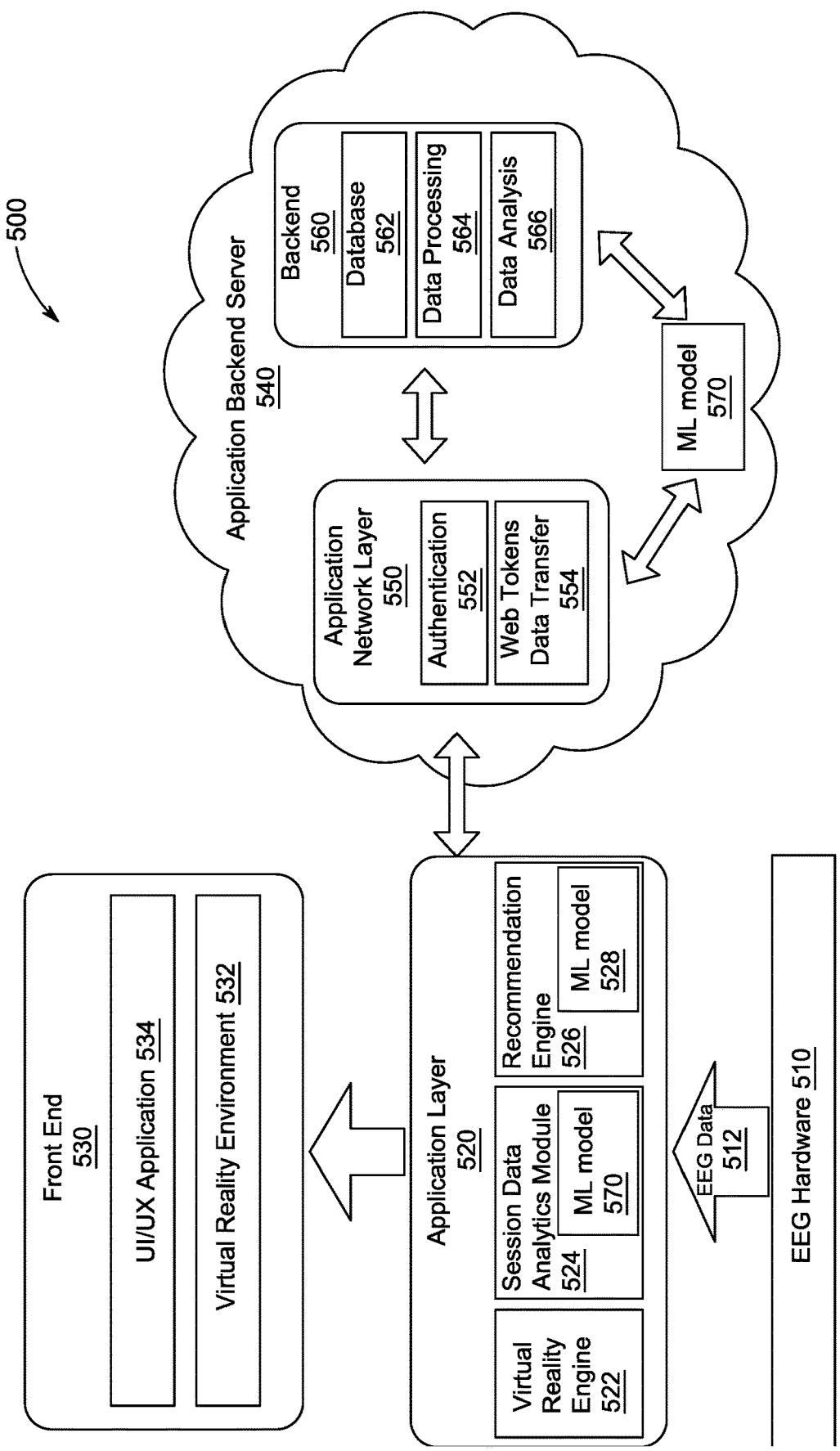
FIG. 5 shows a system architecture to provide audio and/or visual feedback to the user based on brainwave signal measurements.

FIG. 5 shows a system architecture to provide audio and/or visual feedback to the user based on brainwave signal measurements. The system 500 includes the hardware layer 510, the application layer 520, the front end 530, and the application backend server 540.

The hardware layer 510 can include a sensor to continually obtain a brainwave signal of the user. The sensor can include the electroencephalography (EEG) hardware which gathers the brainwave signals of the user, as described in this application. The measured brainwave signals 512 can be passed to the application layer 520.

The application layer 520 can include an optional virtual-reality engine 522, session data analytics module 524, and a recommendation engine 526. The virtual-reality engine 522 can track the user's gaze and render an appropriate visual and audio environment for the user. The session data analytics module 524 can interpret the brainwave signals 512 received from the hardware layer 510 to determine the mental state of the user. The session data analytics module 524 can include an optional machine learning model 570 which can perform the mapping between the brainwave signals 512 into the mental states of the user. The recommendation engine 526 along with the application backend server 540 can determine the desired mental state of the user. To make the determination, the recommendation engine 526 can use an optional machine learning model 528, as described in this application. As a result, the system 500 can induce the desired mental state of the user by providing visual feedback and audio feedback to the user indicating the proximity of the latest determined mental state to the desired mental state.

The front end 530 can include a display to provide visual feedback to the user, and an audio emitter to provide audio feedback to the user. The display in the audio emitter can be part of a virtual reality (VR) environment 532, an augmented reality (AR) environment, or can be independent of the VR/AR. The display can present the user interface of an application 534. The user interface can show various user controllable elements, such as the flame or the waves is described in this application. The audio emitter can play soothing or agitating sounds at various intensities depending on the desired feedback of the user.

The application backend server 540 can include an application network layer 550 and a backend 560. The application backend server 540 can be hosted on a cloud platform. The application network layer 550 can include an authentication module 552 and a web token/data transfer module 554. The authentication module 552 can require and verify an authentication before granting access to the information contained in the backend 560. Upon valid authentication, the web token/data transfer module 554 can transmit data requests and data between the backend 560 and the application layer 520. The backend 560 can contain a database 562, a data processing module 564, and a data analysis module 566. The database 562 can contain brainwave signals gathered from all the users of the system and/or mental states corresponding to the brainwave signals. The data processing module 564 can prepare the brainwave signals for detailed analysis by the data analysis module 566. For example, the data processing module 564 can perform low-pass or high-pass filtering of the brainwave signals. The data analysis module 566 can analyze the data contained in the database 562, identify similar groups of users, identify proficiency levels associated with various groups of users, improve identification of mental states corresponding to the brainwave signals, etc.

The application backend server 540 can also train the machine learning model 570 to identify mental states from brainwave signals and their corresponding mental states stored in the database 562. One or more processors associated with the application backend server 540 can obtain the brainwave signals and the corresponding mental states. To train the machine learning model 570, the processor can provide the brainwave signal to the machine learning model 570, and receive from the machine learning model 570, the mental states output by the machine learning model 570 as associated with the input brainwave signals.

The processor can improve the machine learning model 570 by comparing the output mental states produced by the machine learning model 570 to the corresponding plurality of mental states. When the corresponding mental state and the mental state output by the machine learning model 570 are the same, the processor can provide positive feedback to the machine learning model 570, thus positively reinforcing the pathways within the machine learning model 570 used to reach the mental state output. With the corresponding mental state and the mental state output by the machine learning model 570 being different, the processor can provide negative feedback to the machine learning model 570, thus negatively reinforcing the pathways within the machine learning model 570 used to reach the mental state output. In one embodiment, the mental states in the brainwave signals used to train the machine learning model 570 do not include the brainwave signals and mental states of the user currently being monitored.

The trained machine learning model 570 can be used within the session data analytics module 524 of the application layer 520. The session data analytics module 524 can use the machine learning model 570 to determine whether the brainwave signal received from the hardware layer 510 corresponds to an unfocused mental state or a tense mental state. In response to determining that the mental state corresponds to an unfocused mental state, the application layer 520 can increase the relative intensity of the audio feedback compared to the visual feedback provided to the user in the front end 530. In response to determining that the mental state comprises a tense mental state, the application layer 520 can increase the relative intensity of the visual feedback compared to the audio feedback. As explained in this application, increasing sound intensity and/or radiation can cause an unfocused mental state, while increasing intensity and/or variation of the visual feedback can cause a tense mental state. As a result, the application layer 520 can strike the right balance between visual and sound feedback to induce mindfulness.

The application backend server 540 can obtain a brainwave signal from users experienced in maintaining the desired mental state and store them in the database 562. For example, the users could be monks and meditation experts who have decades of experience mastering meditative introspective and contributive practices to establish meditative states. The application layer 520 along with the application backend server 540 can determine the proficiency of the user in controlling their mental state by comparing the brainwave signals of the user to the brainwave signals of the expert users. The comparison can be done in real-time by comparing the user's proximity to a desired peak mental state in relation to the expert's model. The system determines the optimal stimuli to feedback to the user based on this computation. Another comparison can be done by comparing a percentage of time that the user spends in the desired mental state to the percentage of time that the expert users spent in the desired mental state. The application layer 520 can calibrate the user's proficiency, i.e., the user's cognitive and emotional proficiency and suggest practices and techniques, such as breathing exercises, mantras, and prayers that help the user experience higher meditative states.

The mental state of the user can include a cognitive level of the user or an emotional level of the user. The cognitive level of the user includes focus in memory. The application layer 520 can determine the cognitive level of the user by providing a cognitive test to the user including a memory test and/or a problem-solving test. The application layer 520 can compare the cognitive level of the user to a desired cognitive level. The desired cognitive level can be an average of all the measured users, an average of all the healthy measured users, an average of all the users similar to the current user, etc. Based on the comparison, the application layer 520 can determine whether to recommend to the user to improve their cognitive level.

The application layer 520 can determine the emotional state of the user by providing a trigger intended to evoke a particular emotional state, measuring the brainwave signal of the user in response to the trigger, and determining the emotional state of the user based on the brainwave signal. The trigger intended to evoke the particular emotional state can be a clip from a horror movie to trigger fear or a clip from a comedy to trigger joy. Other triggers can be found by measuring a response from all the users of the trigger, if the response from most of the users is the same, such as 90% or more of the users experience the same emotion, then, the triggers in the particular emotional state can be used together.

The application layer 520 can compare the particular emotional state and the emotional state of the user. Based on the comparison, the application layer 520 can determine whether to recommend to the user to improve their emotional state. For example, if the user does not experience the particular emotional states in response to the trigger, the system can detect an emotional issue of the user. The recommendation engine 526 can suggest to the user to consume various triggers intended to evoke the particular emotion and to practice feeling the particular emotion. For example, if the user does not experience joy in response to a funny audio trigger or a funny audio/visual trigger, the recommendation engine 526 can suggest to the user to view other triggers associated with joy and practice feeling joy in response.

Figure 6:
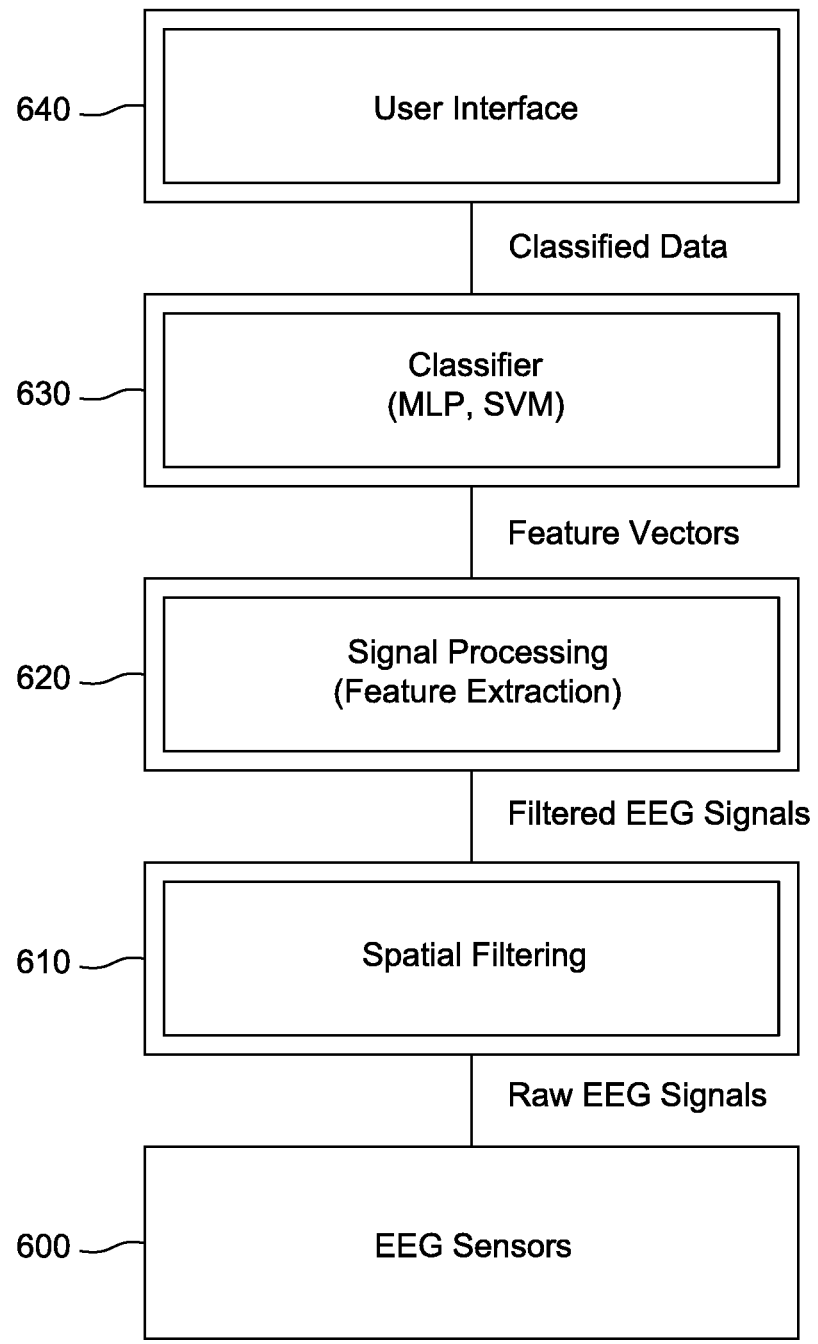
FIG. 6 shows a part of a system and steps performed by the hardware layer, application layer and the front end in FIG. 5, according to one embodiment.

FIG. 6 shows a part of a system and steps performed by the hardware layer, application layer, and the front end in FIG. 5, according to one embodiment. The EEG sensors 600 can be part of the hardware layer 510 in FIG. 5. The EEG sensors 600 measure the brainwave signal of the user and pass the measured brainwave signal to the application layer 520 in FIG. 5, which can perform the steps of spatial filtering 610, signal processing 620, and classification 630. The resulting classified data is passed to the front and application layer 520 in FIG. 5 and presented to the user through the user interface 640.

Steps 610, 620, and 630 can be performed with a machine learning model 570 in FIG. 5. Alternatively, or in addition, step 610 and/or step 620 can be performed as a preprocessing step to prepare the input for the machine learning model 570. For example, in step 610, the system can determine a noise level brainwave signal that the user produces without being provided any kind of visual and/or audio input. When the system provides audio and/or visual input to the user, the noise brainwave signal can be removed from the raw EEG signal using low-pass, high-pass, and/or bandpass filtering.

In step 620, relevant features of the filtered EEG signal can be extracted, such as features corresponding to alpha, beta, theta, and/or delta waves. The feature vectors can be passed to the classifier, which can be a machine learning model, such as a multilayer perceptron (MLP) feedforward artificial neural network or a support vector machine (SVM) learning model.

Figure 7:
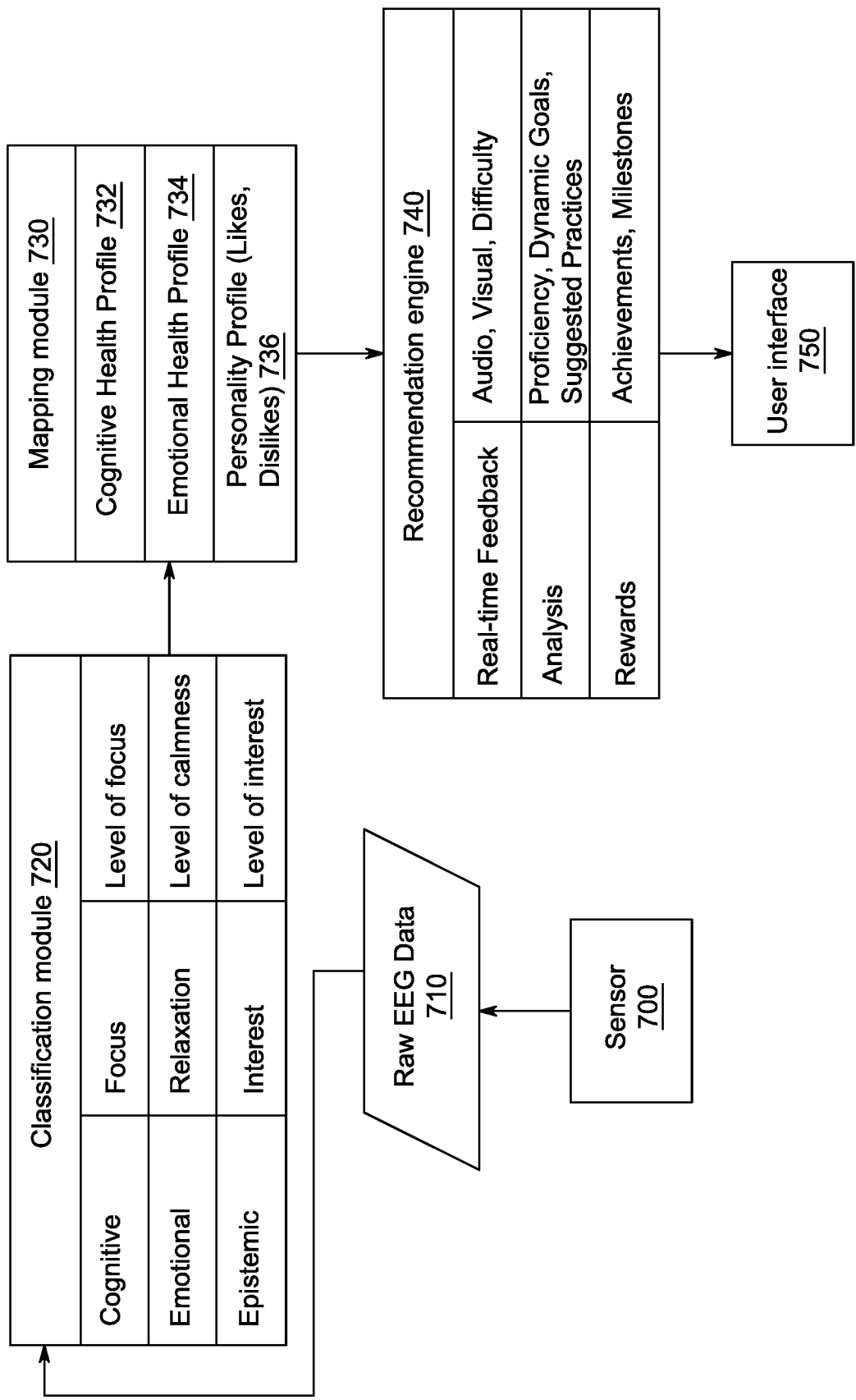
FIG. 7 shows a part of a system and steps performed by the hardware layer, application layer and the front end in FIG. 5, according to another embodiment.

FIG. 7 shows a part of a system and steps performed by the hardware layer, application layer, and the front end in FIG. 5, according to another embodiment. The system includes the brainwave sensor 700, raw EEG data 710, classification module 720, mapping module 730, recommendation engine 740, and the user interface 750. The brainwave sensor 700 provides raw EEG data 710 to a classification module 720.

The classification module 720 can be a machine learning model 570 in FIG. 5 or a software algorithm without a machine learning component. The classification module 720 can classify the received EEG data 710 into various mental states such as cognitive, emotional, and epistemic mental states. For example, the cognitive mental state can be indicated by focus, the emotional mental state can be indicated by relaxation, and the epistemic mental state can be indicated by interest. The classification module 720 can also determine a level of focus, calmness, and/or interest based on the received EEG data 710.

The mapping module 730 can receive the classified mental state from the classification module 720 and the intensity level of the mental state, and create a user profile, such as a cognitive health profile 732, emotional health profile 734, and/or personality profile 736. Based on the various profiles, the mapping module 730 can group similar users together, and use the so created groups for performance comparison, as described in this application.

The recommendation engine 740 can receive the various profiles 732, 734, and 736 from the mapping module 730 and perform various actions based on the received profiles. The recommendation engine 740 can adjust the audio/visual feedback provided to the user in real time to increase or decrease the difficulty of achieving the desired mental state. For example, if the user's cognitive health profile 732 has improved, and the user has reached a higher level of cognitive health, the audio/visual feedback can be adjusted to increase the difficulty of achieving the desired mental state. The visual feedback intensity and/or variety can be increased, while the intensity and/or variety of the audio feedback can be reduced.

The recommendation engine 740 can provide a recommendation to the user by suggesting the determined proficiency, suggesting new dynamic goals, suggesting practices for improving the user's proficiency, etc. Further, the recommendation engine 740 can provide reports to the user by tracking user's progress and indicating the user's improvements, achievements, milestones, etc.

FIG. 8 shows various services provided by the system. The meditation module 800 can analyze data from an EEG sensor and guide the user's meditation accordingly. The cognitive health tracking module 810 can record a user's cognitive health, such as attention, memory, and learning over a predetermined period of time, such as a month, and can provide analysis, tips, and/or a journal. The emotion health tracking module 820 can record user's mental health such as emotions and stressors over a predetermined period of time, such as a month, and can provide analysis, tips, and/or journal. The recovery/skill mastery module 830 can address specific mental or cognitive health goals with emotion and cognitive health, tracking and provide further guidance, and analysis focused on a health or performance goal, such as mastering flow, mindfulness, etc. The platform can be a long-term replacement to costly and marginally effective pharmaceutical drugs, such as stimulants like Adderall for ADHD, anticonvulsants like value procedures, and selective serotonin reuptake inhibitors (SSRIs) like Lexapro for depression. For healthy individuals, it serves as a gym for their brain as they train their brain to achieve higher and higher mental and cognitive capabilities.

FIG. 9 shows a value differentiation of the current system. The current system provides improvements over already existing technology. For example, meditation applications are gimmicky and are not rooted in scientifically tested and validated methods. By contrast, the current system can provide more precise neural feedback, can integrate audio and visual feedback, and can provide a guided meditation session, which results in a more personalized and successful experience.

Organizations don't have a direct way of assessing performance or providing effective interventions for proof improving performance. The current system can improve the performance of individuals by tracking and measuring cognitive and emotional mental states and providing a low stress environment, thus improving the cognitive and emotional states.

Educational institutions don't have a direct way of accessing performance or providing effective interventions for improving performance. The current system can improve performance of users and standardized tests, such as SAT, GMAC, grades, job placement, etc. by lowering stress and improving the mood of users.

Posttraumatic stress disorder treatment is too costly and ineffective. Users of the current system can have improved day-to-day life because of the lower frequency, duration, and strength of flashback episodes because of the training and controlling their emotions the users received while using the system.

Alzheimer's treatment is too costly and ineffective. Users of the current system have better cognitive performance including memory, attention, learning, and improved day-to-day life because of the training and feedback they receive while using the system.

Athletes lack the technology to quantify athletic performance and improve mental resilience readiness. Users of the current system can have better mental fitness and better overall performance due to practicing increasing their focus while using the system.

Figure 10:
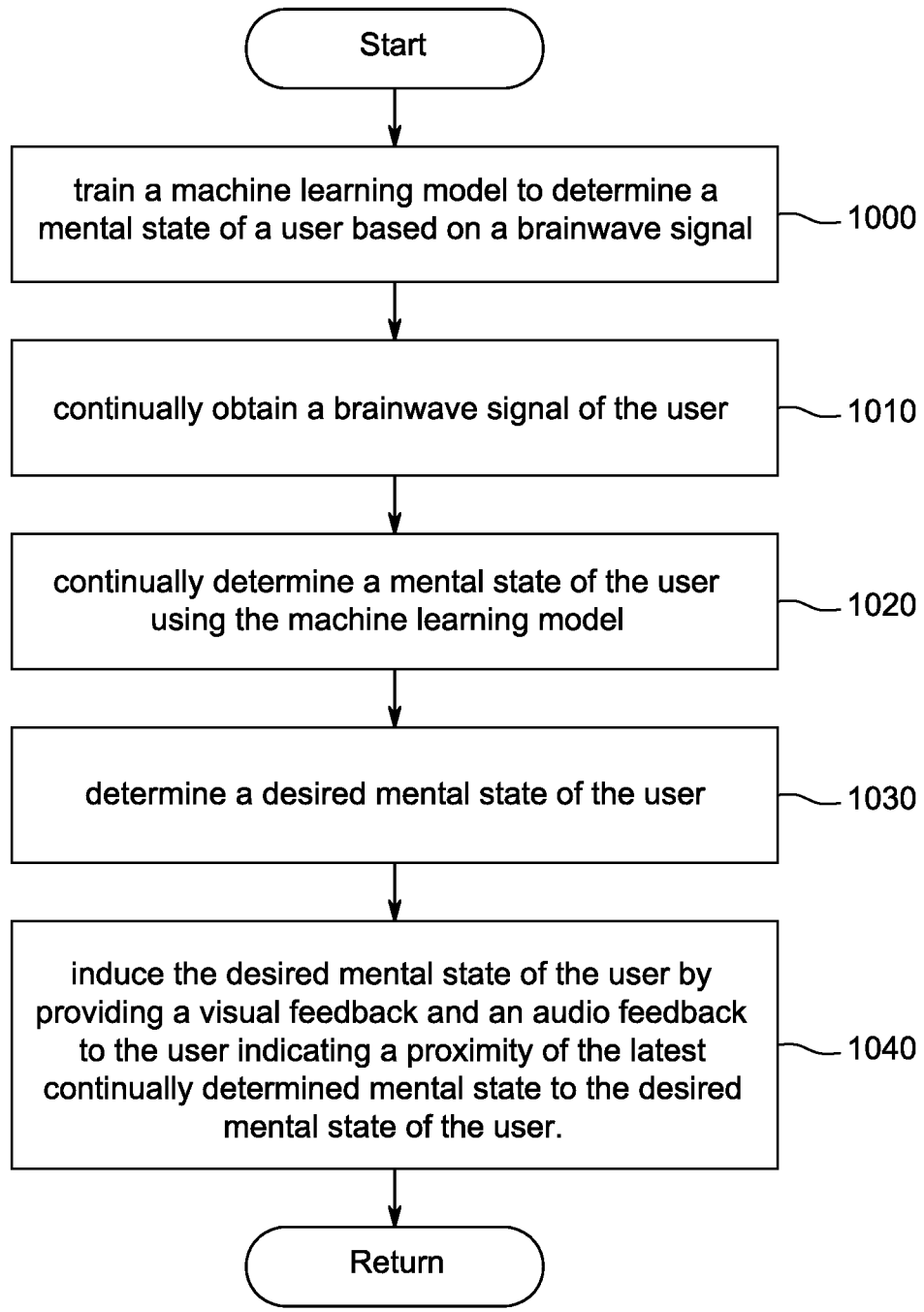
FIG. 10 is a flowchart of a method to induce a desired mental state of a user, according to one embodiment.

FIG. 10 is a flowchart of a method to induce a desired mental state of a user, according to one embodiment. In step 1000, the processor can train the machine learning model to determine the mental state of the user based on the brainwave signal. To train the machine learning model, the processor can obtain brainwave signals and corresponding mental states considered to correctly identify the mental states of the brainwave signals. To obtain the corresponding mental states, the processor can obtain a brainwave signal from a user, and present a query to the user asking the user to identify his or her mental state, such as happy, sad, focused, relaxed, interested, etc. The user provided mental state can then be included in the corresponding mental states.

The processor can provide brainwave signals to the machine learning model. The machine learning model can process the brainwave signals and provide to the processor mental states that the machine learning model has identified as associated with the brainwave signals. The processor can improve the machine learning model by comparing the mental states produced by the machine learning model to the corresponding mental states obtained initially and can provide feedback to the machine learning model based on the comparison. For example, if a brainwave signal and its corresponding mental state are the same as the mental states produced by the machine learning model based on the brainwave signal, the processor can provide positive feedback to the machine learning model to strengthen the weights of the neuron connections that have produced the correct mental state. Conversely, if the corresponding mental state of a brainwave signal is not the same as the mental state produced by the machine learning model based on the brainwave signal, the processor can provide negative feedback to the machine learning model to weaken the weights of the neuron connections that have produced the incorrect mental state.

In step 1010, the processor can continually obtain the brainwave signal of the user from a sensor attached to the user side, such as an EEG sensor. In step 1020, the processor can continually determine the mental state of the user using the machine learning model. The mental state can include cognitive, emotional, and/or epistemic states.

In step 1030, the processor can determine the desired mental state of the user. The desired mental state of the user can be specified by the user, or can be determined based on external factors, such as day of the week, time of day, history of desired mental states provided by the user, etc. In one embodiment, a machine learning model can be used to determine the desired mental state. In another embodiment, the processor can obtain mental states from users by measuring brainwave signals of the users. The users can be healthy users of the system. The processor can average the mental states of the healthy users to obtain the desired mental state.

In step 1040, the processor can induce the desired mental state of the user by providing visual feedback and audio feedback to the user indicating a proximity of the latest continually determined mental state to the desired mental state of the user.

Figure 11:
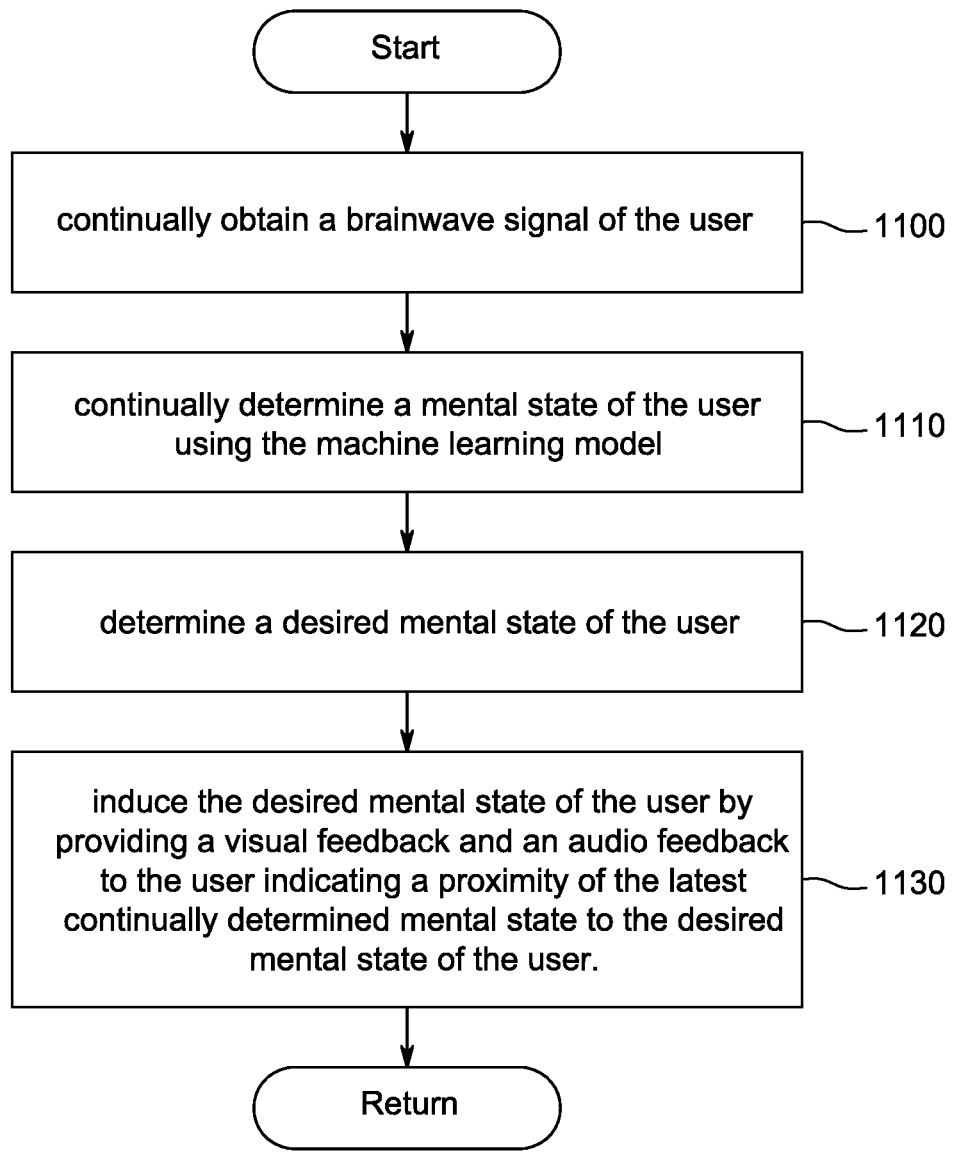
FIG. 11 is a flowchart of a method to induce a desired mental state of a user, according to another embodiment.

FIG. 11 is a flowchart of a method to induce a desired mental state of a user, according to another embodiment. In step 1100, the processor can continually obtain the brainwave signal of the user. In step 1110, based on the obtained brainwave signal of the user, the processor can continually determine the mental state of the user. To determine the mental state of the user, the processor can use train a machine learning model to produce a mental state given a brainwave signal. The processor can utilize the trained machine learning model by providing the brainwave signal of the user to the machine learning model and receiving the mental state as output. To obtain the training set, the processor can measure brainwave signals of users different from the current user and ask the users to provide their mental state when the brainwave signals are measured.

In step 1120, the processor can determine the desired mental state of the user. In one embodiment, to determine the desired mental state of the user, the processor can obtain a time of day, a current mental state of the user, and previously specified desired mental states. Based on at least one of the previously listed parameters, the processor can determine the desired mental state of the user. In another embodiment, to determine the mental state of the user, the processor can train an artificial intelligence model to predict the desired mental state of the user by making a prediction regarding the desired mental state and receiving an input from the user specifying the desired mental state. The processor can improve the machine learning model based on the prediction and the specified desired mental state. To make the prediction, the machine learning model can take into account the time of day, the current mental state of the person, the history of previously desired mental states, etc.

In step 1130, the processor can induce the desired mental state of the user by providing visual feedback and audio feedback to the user indicating a proximity of the latest determined mental state to the desired mental state.

The processor can determine whether the mental state includes an unfocused mental state or a tense mental state. In response to determining that the mental state includes the unfocused mental state, the processor can increase the relative intensity of the audio feedback compared to the visual feedback. In response to determining that the mental state includes the tense mental state, the processor can increase the relative intensity of the visual feedback compared to the audio feedback.

The processor can obtain brainwave signals from multiple users experienced in maintaining the desired mental state. The users can be monks and meditation experts who have decades of experience mastering meditative introspective and contributive practices to establish meditative states. The processor can determine the proficiency of the user in controlling the mental state by comparing the brainwave signal of the user to the brainwave signals from the plurality of users experienced in maintaining the desired mental state. Based on the comparison, the processor can calibrate the user's cognitive and emotional proficiency and suggest practices and techniques, such as breathing exercises, mantras, and prayers that help the user experience higher meditative states.

The comparison can be done by, for example, comparing a percentage of time that the user spends in the desired mental state as compared to the experienced users. For example, to make the comparison, the processor can compare a normalized amount of time the user spent in the desired mental state and an average normalized amount of time the plurality of users experienced in maintaining the desired mental state spent in the desired mental state. The normalized amount of time can be the total time spent in the desired mental state expressed as a fraction or percentage of the total time spent using the system.

The processor can increase the proficiency of the user by dynamically adjusting the difficulty of obtaining the desired mental state by adjusting at least one of the following intensity of the audio feedback, the intensity of the visual feedback, the type of the audio feedback, or the type of the visual feedback. The type of audio and visual feedback can vary between stormy weather versus rolling waves, battle scene versus a moonlit night, etc. The processor can incorporate dynamic difficulty adjustment to ensure the challenge of the experience is suited to the user's skill level. The processor can measure the user's level of interest and engagement and tailor the experience accordingly. For example, the necessary level of focus and relaxation needed for the user to make the flame brighter and rather calmer, as described in FIG. 2A, can be dynamically adjusted based on the user skill level and the challenge level of the game. The end result of the experience can be induced states of flow in the user. To avoid overwhelming the user, the processor can adjust the maximum amount of intensity, i.e., challenge, for each user based on the user skill level.

The processor can determine the cognitive level of the user by providing a cognitive test to the user, such as a memory test or a problem-solving test. The processor can compare the cognitive level of the user to the desired cognitive level. The desired cognitive level can be an average of all the measured users or an average of all the healthy measured users. Based on the comparison, the processor can determine whether to recommend to the user to improve the cognitive level of the user. For example, if the user's cognitive level is lower than the desired cognitive level, the processor can make a recommendation to the user to work on the cognitive level.

The processor can determine the emotional state of the user by providing a trigger intended to evoke a particular emotional state. The processor can measure the brainwave signal of the user in response to the trigger, and can determine the emotional state of the user based on the brainwave signal. The particular emotional state can be measured as an average response from all the users or all healthy users. The processor can compare the particular expected emotional state and the emotional state of the user. Based on the comparison, the processor can determine whether to recommend to the user to improve his or her emotional state.

For example, the processor can continuously learn about an individual's baseline emotional state by having the user watch and listen to videos and music that are meant to trigger specific emotions. A clip from a horror movie has a high probability of triggering a fear baseline, a clip from a comedy has a high probability of triggering a joy baseline, etc. if the user does not experience the expected motion, the system can suggest to the user to practice various emotional states by watching various clips within the system. Other triggers can be found by measuring a response from all the users to the trigger, and if the response from most of the users is the same, such as 90% or more of the users experience the same emotion, then, the trigger and the particular emotional state can be used together.

The processor can display an indication of the current stressor of the user to the user. The processor can interpret the brainwave signal of the user as controlling a movable element within the display, such as the waves 320 in FIG. 3A. The movable element can at least partially remove the indication of the current stressor. The processor can remove the indication of the current stressor as the brainwave signal of the user achieve, the desired brainwave signal, or as the user maintains the desired mental state for the desired period of time. To challenge the user, the processor can provide triggers that evoke the negative emotion. For example, the weather and waves can take on the quality of the stressor. As the user comes closer to the desired mental state or as the user maintains the desired mental state for the desired amount of time, the weather and waves can subside and take on positive and soothing qualities. The processor can establish a maximum intensity threshold for the negative stimulus in order to prevent the feedback from overwhelming the user. Upon successful washing away, users will be rewarded with soothing sounds and pleasant colors as the waves receding back into the ocean. The goal is to wash away negative mental states.
Computer FIG. 12 is a diagrammatic representation of the machine in the example form of the computer system 1200, within which a set of instructions for causing the machine to perform any one or more of the methodologies or modules discussed herein, may be executed.

Figure 12:
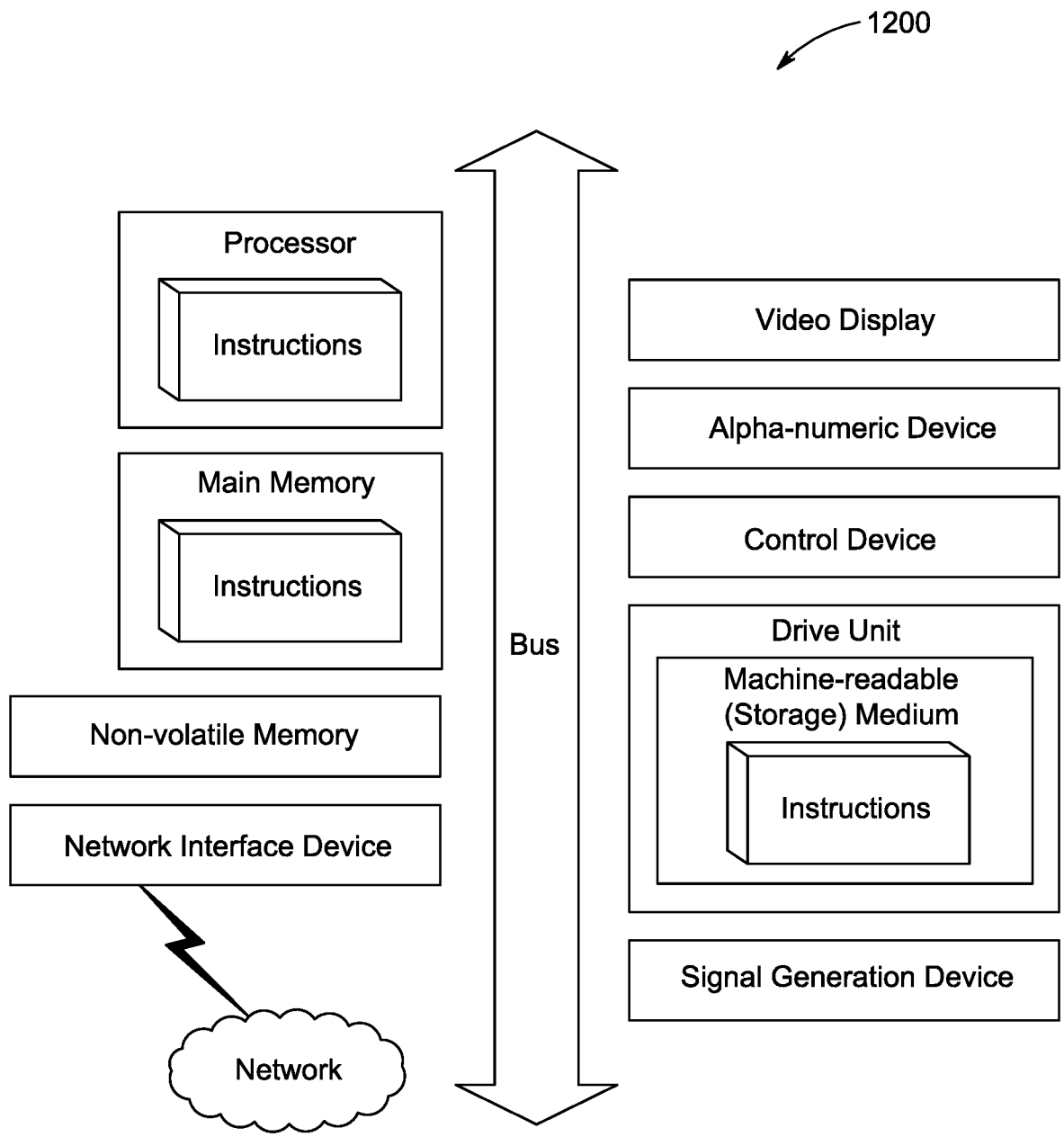
FIG. 12 is a diagrammatic representation of a machine in the example form of a computer system 1200 within which a set of instructions, for causing the machine to perform any one or more of the methodologies or modules discussed herein, may be executed.

In the example of FIG. 12, the computer system 1200 includes a processor, memory, non-volatile memory, and an interface device. Various common components (e.g., cache memory) are omitted for illustrative simplicity. The computer system 1200 is intended to illustrate a hardware device on which any of the components described in the example of FIGS. 1-11 (and any other components described in this specification) can be implemented. The computer system 1200 can be of any applicable known or convenient type. The components of the computer system 1200 can be coupled together via a bus or through some other known or convenient device.

The processor in FIG. 12 can be the processor performing various functions described in this application, such as the functions described in FIGS. 10-11. The processor in FIG. 12 can be the processor associated with the EEG hardware 510 in FIG. 5, the application layer 520 in FIG. 5, the front-end 530 in FIG. 5, and/or the application backend server 540 in FIG. 5. The processor can be used to train the machine learning model described in this application, or can be used to run the machine learning models. The processor can be associated with an AR, VR sets, or can be associated with a device providing video/audio feedback to the user. The display in FIG. 12 can be the display providing the visual feedback to the user.

This disclosure contemplates the computer system 1200 taking any suitable physical form. As example and not by way of limitation, computer system 1200 may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, or a combination of two or more of these. Where appropriate, computer system 1200 may include one or more computer systems 1200; be unitary or distributed; span multiple locations; span multiple machines; or reside in a cloud, which may include one or more cloud components in one or more networks. Where appropriate, one or more computer systems 1200 may perform without substantial spatial or temporal limitation one or more steps of one or more methods described or illustrated herein. As an example, and not by way of limitation, one or more computer systems 1200 may perform in real time or in batch mode one or more steps of one or more methods described or illustrated herein. One or more computer systems 1200 may perform at different times or at different locations one or more steps of one or more methods described or illustrated herein, where appropriate.

The processor may be, for example, a conventional microprocessor, such as an Intel Pentium microprocessor or Motorola power PC microprocessor. One of skill in the relevant art will recognize that the terms "machine-readable (storage) medium" or "computer-readable (storage) medium" include any type of device that is accessible by the processor.

The memory is coupled to the processor by, for example, a bus. The memory can include, by way of example but not limitation, random access memory (RAM), such as dynamic RAM (DRAM) and static RAM (SRAM). The memory can be local, remote, or distributed.

The bus also couples the processor to the non-volatile memory and drive unit. The non-volatile memory is often a magnetic floppy or hard disk, a magnetic-optical disk, an optical disk, a read-only memory (ROM), such as a CD-ROM, EPROM, or EEPROM, a magnetic or optical card, or another form of storage for large amounts of data. Some of this data is often written, by a direct memory access process, into memory during execution of software in the computer 1200. The non-volatile storage can be local, remote, or distributed. The non-volatile memory is optional because systems can be created with all applicable data available in memory. A typical computer system will usually include at least a processor, memory, and a device (e.g., a bus) coupling the memory to the processor.

Software is typically stored in the non-volatile memory and/or the drive unit. Indeed, storing and entire large program in memory may not even be possible. Nevertheless, it should be understood that for software to run, if necessary, it is moved to a computer readable location appropriate for processing, and for illustrative purposes, that location is referred to as the memory in this paper. Even when software is moved to the memory for execution, the processor will typically make use of hardware registers to store values associated with the software, and local cache that, ideally, serves to speed up execution. As used herein, a software program is assumed to be stored at any known or convenient location (from non-volatile storage to hardware registers) when the software program is referred to as "implemented in a computer-readable medium." A processor is considered to be "configured to execute a program" when at least one value associated with the program is stored in a register readable by the processor.

The bus also couples the processor to the network interface device. The interface can include one or more of a modem or network interface. It will be appreciated that a modem or network interface can be considered to be part of the computer system 1200. The interface can include an analog modem, isdn modem, cable modem, token ring interface, satellite transmission interface (e.g., "direct PC"), or other interfaces for coupling a computer system to other computer systems. The interface can include one or more input and/or output devices. The I/O devices can include, by way of example but not limitation, a keyboard, a mouse or other pointing device, disk drives, printers, a scanner, and other input and/or output devices, including a display device. The display device can include, by way of example but not limitation, a cathode ray tube (CRT), liquid crystal display (LCD), or some other applicable known or convenient display device. For simplicity, it is assumed that controllers of any devices not depicted in the example of FIG. 12 reside in the interface.

In operation, the computer system 1200 can be controlled by operating system software that includes a file management system, such as a disk operating system. One example of operating system software with associated file management system software, is the family of operating systems known as Windows® from Microsoft Corporation of Redmond, Wash., and their associated file management systems. Another example of operating system software with its associated file management system software is the Linux™ operating system and its associated file management system. The file management system is typically stored in the non-volatile memory and/or drive unit and causes the processor to execute the various acts required by the operating system to input and output data and to store data in the memory, including storing files on the non-volatile memory and/or drive unit.

Some portions of the detailed description may be presented in terms of algorithms and symbolic representations of operations on data bits within the computer memory. These algorithmic descriptions and representations are the means used by those skilled in the data processing arts to most effectively convey the substance of their work to others skilled in the art. An algorithm is here, and generally conceived to be a self-consistent sequence of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms, such as "processing," "computing," "calculating," "determining," "displaying," "generating," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission, or display devices.

The algorithms and displays presented herein are not inherently related to any particular computer or other apparatus. Various general-purpose systems may be used with programs in accordance with the teachings herein, or it may prove convenient to construct more specialized apparatus to perform the methods of some embodiments. The required structure for a variety of these systems will appear from the description below. In addition, the techniques are not described with reference to any particular programming language, and various embodiments may thus be implemented using a variety of programming languages.

In alternative embodiments, the machine operates as a standalone device or may be connected (e.g., networked) to other machines. In a networked deployment, the machine may operate in the capacity of a server or a client machine in a client-server network environment, or as a peer machine in a peer-to-peer (or distributed) network environment.

The machine may be a server computer, a client computer, a personal computer (PC), a tablet PC, a laptop computer, a set-top box (STB), a personal digital assistant (PDA), a cellular telephone, an iPhone, a Blackberry, a processor, a telephone, a web appliance, a network router, switch or bridge, or any machine capable of executing a set of instructions (sequential or otherwise) that specify actions to be taken by that machine.

While the machine-readable medium or machine-readable storage medium is shown in an exemplary embodiment to be a single medium, the term "machine-readable medium" and "machine-readable storage medium" should be taken to include a single medium or multiple media (e.g., a centralized or distributed database, and/or associated caches and servers) that store the one or more sets of instructions. The term "machine-readable medium" and "machine-readable storage medium" shall also be taken to include any medium that is capable of storing, encoding, or carrying a set of instructions for execution by the machine and that cause the machine to perform any one or more of the methodologies or modules of the presently disclosed technique and innovation.

In general, the routines executed to implement the embodiments of the disclosure, may be implemented as part of an operating system or a specific application, component, program, object, module, or sequence of instructions referred to as "computer programs." The computer programs typically comprise one or more instructions set at various times in various memory and storage devices in a computer, and that, when read and executed by one or more processing units or processors in a computer, cause the computer to perform operations to execute elements involving the various aspects of the disclosure.

Moreover, while embodiments have been described in the context of fully functioning computers and computer systems, those skilled in the art will appreciate that the various embodiments are capable of being distributed as a program product in a variety of forms, and that the disclosure applies equally regardless of the particular type of machine or computer-readable media used to actually effect the distribution.

Further examples of machine-readable storage media, machine-readable media, or computer-readable (storage) media include, but are not limited to, recordable type media, such as volatile and non-volatile memory devices, floppy and other removable disks, hard disk drives, optical disks (e.g., Compact Disk Read-Only Memory (CD ROMS), Digital Versatile Disks, (DVDs), etc.), among others, and transmission type media, such as digital and analog communication links.

In some circumstances, operation of a memory device, such as a change in state from a binary one to a binary zero or vice-versa, for example, may comprise a transformation, such as a physical transformation. With particular types of memory devices, such a physical transformation may comprise a physical transformation of an article to a different state or thing. For example, but without limitation, for some types of memory devices, a change in state may involve an accumulation and storage of charge or a release of stored charge. Likewise, in other memory devices, a change of state may comprise a physical change or transformation in magnetic orientation or a physical change or transformation in molecular structure, such as from crystalline to amorphous or vice-versa. The foregoing is not intended to be an exhaustive list in which a change in state from a binary one to a binary zero or vice-versa in a memory device may comprise a transformation, such as a physical transformation. Rather, the foregoing are intended as illustrative examples.

A storage medium typically may be non-transitory or comprise a non-transitory device. In this context, a non-transitory storage medium may include a device that is tangible, meaning that the device has a concrete physical form, although the device may change its physical state. Thus, for example, non-transitory refers to a device remaining tangible despite this change in state.

The language used in the specification has been principally selected for readability and instructional purposes, and it may not have been selected to delineate or circumscribe the inventive subject matter. It is therefore intended that the scope of the invention be limited not by this Detailed Description, but rather by any claims that issue on an application based hereon. Accordingly, the disclosure of various embodiments is intended to be illustrative, but not limiting, of the scope of the embodiments, which is set forth in the following claims.

What is claimed is:

1. A system for mental training of a user, the system comprising:
   at least one computing device;
   at least one bio-signal sensor operably coupled to the computing device, the at least one bio-signal sensor configured into a headgear shaped to be worn by the user, the bio-signal sensor configured to receive a brain's electrical activity data from the user;
   at least one user's input device operably coupled to the computing device; at least one output device operably coupled to the computing device;
   the computing device comprising a memory and a processor, the memory comprising a set of instruction that, when executed by the processor, causes the processor to:
   receive a user's profile and a desired mental state from the user's input device, the user's profile comprising user's past performance in the mental training, user's interests, and effects of emotional triggers on the user;
   receive, in near real-time, a brain's electrical activity data in response to a mental act being performed by the user, from the at least one bio-signal sensor;
   process the brain's electrical activity data to one or more features, the one or more features related to emotional and cognitive mental states of the user while performing the mental act;
   process the one or more features to a measured mental state;
   present, in near real-time, an interactive simulated environment to the user while performing the mental act based on the one or more features and a difference of the measured mental state with the desired mental state, wherein the simulated environment comprises:
   a flame of varying color, intensity, and flickering, wherein the color, intensity, and flickering are selectively varied based on the one or more features and the difference;
   sound of wind varying in intensity, wherein the intensity of the flame and the wind in the interactive simulated environment is balanced to induce the desired mental state;
   wherein the computing device is further configured to: store the data related to the measured mental state; analyze the stored data to determine improvement data, the improvement data comprising graphical representations;
   presenting a three-dimensional graph, the graph comprises: a wanderer zone, indicating a relaxed state of mind, a mindfulness zone, indicating a desired mental state, a stress zone, indicating focus a mental state, and a curve indicating durations of the relaxed state of mind, desired mental state, and focused mental state; and presenting the improvement data to the user.

2. The system of claim 1, wherein the at least one bio-signal sensor is an EEG sensor.

3. The system of claim 1, wherein the measured mental state is in response to an emotional activity of the user.

4. The system of claim 3, wherein the emotional activity is meditation.

5. The system of claim 1, wherein the output device is a virtual reality (VR) headset.

6. The system of claim 1, wherein the measured mental state is in response to a cognitive activity of the user.

7. The system of claim 6, wherein the cognitive activity is learning.

8. The system of claim 1, wherein the system further comprises a galvanic skin response sensor configured to be worn by the user, the galvanic skin response sensor is in communication with the computing device.

9. The system of claim 1, wherein the system further comprises a seismocardiogram sensor configured to be worn by the user, the seismocardiogram sensor is in communication with the computing device.

10. The system of claim 1, wherein the system further comprises an electrocardiogram sensor configured to be worn by the user, the electrocardiograms sensor is in communication with the computing device.

11. The system of claim 1, wherein the system further comprises a ballistocardiogram sensor configured to be worn by the user, the ballistocardiogram sensor is in communication with the computing device.

12. The system of claim 1, wherein the one or more features comprises focus, calmness, distraction, and stress, wherein an increase in focus results in the flame becoming bigger, an increase in the calmness results in the flame becoming steadier, an increase in the stress results in decreasing of the intensity of the flame, and an increase in the distraction results in changing of color of the flame to emerald green or sapphire blue.

13. The system of claim 1, wherein the processor further:
determine a threshold for variations in the interactive simulated environment.

14. A system for mental training of a user, the system comprising:
at least one computing device;
at least one bio-signal sensor operably coupled to the computing device, the at least one bio-signal sensor configured into a headgear shaped to be worn by the user, the bio-signal sensor configured to receive a brain's electrical activity data from the user;
at least one user's input device operably coupled to the computing device; at least one output device operably coupled to the computing device;
the computing device comprising a memory and a processor, the memory comprising a set of instruction that, when executed by the processor, causes the processor to:
process the brain's electrical activity data to one or more features, the one or more features related to emotional and cognitive mental states of the user;
process the one or more features to a measured mental state;
receive a desired mental state from the user's input device;
present a simulated environment to the user, the simulated environment comprises:
a foreground and a background, wherein a difference between the foreground and the background indicate a difference between the measured mental state and the desired mental state;
wherein the foreground and the background interacts, the background affects the characteristics of the foreground, the characteristics comprises an intensity of the foreground;

wherein the foreground is a flame and background is weather, the weather affects the intensity of the flame, brighter the flames are, the more is the resistance of the flame to the weather.

15. The system of claim 14, wherein the foreground is a flame and background is weather, the weather affects the intensity of the flame, the weather comprises storm, wherein a larger is the difference between the desired mental state and the measured mental state, the stronger is the weather, the stronger weather weakens the flame.

16. A system for mental training of a user, the system comprising:
at least one computing device;
at least one bio-signal sensor operably coupled to the computing device, the at least one bio-signal sensor configured into a headgear shaped to be worn by the user, the bio-signal sensor configured to receive a brain's electrical activity data from the user;
at least one user's input device operably coupled to the computing device; at least one output device operably coupled to the computing device;
the computing device comprising a memory and a processor, the memory comprising a set of instruction that, when executed by the processor, causes the processor to:
receive a user's profile and a desired mental state from the user's input device, the user's profile comprising user's past performance in the mental training, user's interests, and effects of emotional triggers on the user;
receive, in near real-time, a brain's electrical activity data in response to a mental act being performed by the user, from the at least one bio-signal sensor;
process the brain's electrical activity data to one or more features, the one or more features related to emotional and cognitive mental states of the user while performing the mental act;
process the one or more features to a measured mental state;
present, in near real-time, an interactive simulated environment to the user while performing the mental act based on the one or more features and a difference of the measured mental state with the desired mental state, wherein the simulated environment comprises:
a flame of varying color, intensity, and flickering, wherein the color, intensity, and flickering are selectively varied based on the one or more features and the difference;
sound of wind varying in intensity, wherein the intensity of the flame and the wind in the interactive simulated environment is balanced to induce the desired mental state;
wherein the one or more features comprises focus, calmness, distraction, and stress, wherein an increase in focus results in the flame becoming bigger, an increase in the calmness results in the flame becoming steadier, an increase in the stress results in decreasing of the intensity of the flame, and an increase in the distraction results in changing of color of the flame to emerald green or sapphire blue.

* * * * *